US006255308B1

(12) United States Patent
Russell et al.

(10) Patent No.: US 6,255,308 B1
(45) Date of Patent: *Jul. 3, 2001

(54) TREATMENT OF EQUINE PROTOZOAL MYELOENCEPHALITIS

(75) Inventors: Meri Charm Russell, Des Moines, IA (US); Clara K. Fenger, Lexington, KY (US)

(73) Assignee: Blue Ridge Pharmaceuticals, Inc., Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/069,956

(22) Filed: Apr. 30, 1998

Related U.S. Application Data

(63) Continuation of application No. 08/683,507, filed on Jul. 17, 1996, now Pat. No. 5,747,476.

(51) Int. Cl.[7] .......................... A61K 31/505; A61K 31/18
(52) U.S. Cl. ..................... 514/256; 514/275; 514/601
(58) Field of Search .................................. 514/256, 275, 514/601

(56) References Cited

U.S. PATENT DOCUMENTS

| 3,905,971 | 9/1975 | Miller | 260/247.5 |
|---|---|---|---|
| 4,473,548 | 9/1984 | Frenkel et al. | 424/88 |
| 4,767,760 | 1/1987 | Boeckx et al. | 514/242 |
| 4,952,570 | 11/1989 | Boeckx et al. | 514/242 |
| 5,070,091 | 12/1991 | Mehlhorn et al. | 514/242 |
| 5,114,938 | 1/1990 | Linder et al. | 514/242 |
| 5,141,938 | 8/1992 | Lindner et al. | 514/242 |
| 5,214,043 | 5/1993 | Lindner et al. | 514/242 |
| 5,273,970 | * 12/1993 | McHardy | 514/157 |
| 5,424,310 | 6/1995 | Fukami et al. | 514/242 |
| 5,464,837 | 11/1995 | Mehlhorn et al. | 514/242 |
| 5,747,476 | * 5/1998 | Russell et al. | 514/275 |
| 5,830,893 | 11/1998 | Russell | 514/242 |

FOREIGN PATENT DOCUMENTS

98/43644   10/1998   (WO) .

OTHER PUBLICATIONS

Mayhew, et al., "Protozoal Diseases", The Veterinary Clinics of North America Equine Practice, vol. 2, No. 2, p. 439–459 (Aug. 1986).

Brewer, Barbara W., "Multifocal Neurologic Disease in a Horse"; Equine Veterinary Science, vol. 8, No. 4, p. 302–304 (Apr., 1988).

Kobluk, et al., (eds.) The Horse Diseases & Clinical Management, W.B. Saunders Company, p. 459–462 and pp. 729–730 (1995).

Schoondermark et al., "In vitro effects of sulfadiazine and its metabolites alone and in combination with pyrmethamine on Toxoplasma gondi"; Chemical Abstracts, Vol. 122, p. 570, 122:235089(n) (Mar., 1995).

Fenger, Clara K., "Update on the Diagnosis and Treatment of Equine Protozoal Myeloencephalits (EPM)," Proceedings of the 13th Annual Veterinary Medical Forum, American College of Veterinary Internal Medicine, pp. 597–599 (May, 1995).

Andrews, Frank M. et al., "Differentiating Neurologic Diseases in the Horse Using Albumin Quotient and IgG Index Determination," Proceedings of the 13th Annual Veterinary Medical Forum," American College of Veterinary Internal Medicine, (May, 1995).

Podzamczer, et al., "Twice–weekly maintenance theraphy with sulfa–diazine–pyrimethamine to prevent recurrent toxoplasmic encephalitis in patients with AIDS", I—Pharmacology, Vol. 23, p. 37, 123–102131 (u) (August, 1995).

Clara K. Fenger, Application of the Small Subunit Ribosomal RNA Gene Sequence of Sarcocystis Neurona toward Delineation of the Definitive Host and Serologic Studies (Ph.D. dissertation, The Graduate School, University of Kentucky, Lexington (Mar., 1996)) (believed to be unpublished).

Moore, Bonnie Rush, "Informal Survey of Equine Protozoal Myeloencephalitis," Kansas State University, Mar., 1996.

Bertone, Joseph J, "Update on Equine Protozoal Myeloencephalitis," FDA Vet., Vol. XI, No. III, May/June (May/June 1996).

Fenger, et al., "Epizootic of Equine Protozoal Myeloencephalits on a Farm", Journal of the American Veterinary Medical Association, Vol 210, No. 7, p. 923–927 (Apr. 1997).

* cited by examiner

*Primary Examiner*—Kevin E. Weddington
(74) *Attorney, Agent, or Firm*—Howrey Simon Arnold & White, LLP

(57) ABSTRACT

The present invention relates to compositions and methods for treating equines, such as horses, afflicted with equine protozoal myeloencephalitis or EPM. The therapeutic compositions comprise a combination of pyrimethamine and a sulfonamide, preferably, sulfadiazine, in the absence of known therapeutic amounts of trimethoprim.

29 Claims, No Drawings

TREATMENT OF EQUINE PROTOZOAL MYELOENCEPHALITIS

CROSS REFERENCED TO RELATED APPLICATION

This application is a continuation of U.S. application Ser. No. 08/683,507 filed Jul. 17, 1996 and will issue into U.S. Pat. No. 5,747,476 on May 5, 1998.

FIELD OF THE INVENTION

The present invention relates to compositions and methods for treating equines, such as horses, afflicted with equine protozoal myeloencephalitis or EPM. EPM is a debilitating neurologic disease of equines which can affect the brain, the brain stem, spinal cord, or any combination of these three areas of the equine's central nervous system. EPM is caused by infection by the protozoan parasite *Sarcocystis neurona* (recently referred to as *Sarcocystis falcatula*). There is no vaccine or approved animal drug product available for effectively treating this disease in horses.

BACKGROUND OF THE INVENTION

Although the symptoms and effects of EPM have been recognized since the 1970's, it was not until 1991 that the protozoan parasite that causes EPM was cultured from a horse and given the name *Sarcocystis neurona*. The horse is an aberrant, dead-end host, as infectious forms of the parasite are not passed from horse to horse or from infected horse to a definitive or true intermediate host. Recent investigations indicate that the feces of the opossum (the definitive host) are the source of the infection for horses.

EPM occurs in much of North America. Serologic surveys conducted in central Kentucky, one county in Pennsylvania, and the entire states of Ohio and Oregon, have revealed that approximately fifty percent (50%) of the horses in the surveyed areas have been exposed to the above-noted protozoan parasite. A positive serum test indicates exposure to the parasite, not necessarily the presence of an active form of the disease. The incidence of the active disease is much lower.

In studies that looked at the distribution of seropositive cases geographically, it was found that climatic factors may affect exposure rates; i.e., an increase of freezing days or a very hot environment was associated with a decrease in the numbers of horses exposed to the parasite. EPM appears to have a sporadic distribution, although outbreaks have occurred on farms in Kentucky, Ohio, Indiana, Michigan and Florida.

A horse of any age, breed, or sex may be affected by EPM. The disease has occurred in a horse of two months of age, as well as one in its thirties. In fact, any horse demonstrating neurologic abnormalities should be considered a candidate for EPM affliction.

Clinical signs of the condition depend on the location of the organism within the central nervous system. These signs include weakness, malposition of a limb, muscle atrophy, spinal ataxia, or "wobbling" and/or head tilt with asymmetry of the face (e.g., eyelid, ear, or lip). A severely EPM-affected horse may become recumbent and unable to rise. Lameness not traceable to orthopedic disease or any combination of the above signs may occur with EPM. Other unusual signs may also occur.

In most cases, an affected horse is bright and alert with a normal appetite, although it may be dysphagic (i.e., unable to eat) and may act as if it is choked with feed material coming from its nose. Hematological and biochemical blood values are usually in the normal range.

Diagnosis of EPM is based on clinical signs and on testing of the horse's cerebrospinal fluid (CSF). Originally, the diagnosis was based on the presence of antibodies to *Sarcocystis neurona* in serum, though it is now known that a positive serum test cannot be used to make a diagnosis; such positive serum test simply indicates exposure to the parasite, not necessarily presence of the disease. Cerebrospinal fluid testing is now believed to be the most useful test to assist in the diagnosis of this disease in a live horse.

Currently available treatment of horses with EPM is expensive and typically requires a duration of at least ninety (90) days. In some cases, treatment lasts indefinitely. This current treatment involves the adaptation of tablets intended for human use. Thus, pyrimethamine tablets are administered along with tablets containing a trimethoprim-sulfonamide combination. Typically, the two types of tablets are crushed and placed in suspension for oral administration. These medications should be administered one hour prior to feeding hay and are accompanied with frequent, periodic, veterinary, neurologic examinations during the treatment period.

Discontinuation of therapy is usually based on the administration of medication thirty days beyond the plateau of clinical improvement or disappearance of antibody to the protozoa from the CSF. Suboptimal dosing or intermittent therapy has no proven efficacy.

Adverse effects of therapy may include anemia, abortion, diarrhea and low white blood cell counts. Both medications for treatment of EPM inhibit folic acid metabolism. Unlike horses, however, the protozoan is unable to utilize preformed folic acid. Supplementation with folic acid or folinic acid (40 mg orally, once a day) and/or brewer's yeast may help prevent adverse side effects. It is suggested, however, that folic acid not be administered at the same time as the pyrimethamine because of competitive inhibition and absorption.

The gametocytocidal and sporontocidal effects of 2 g sulfadiazine with 50 mg pyrimethamine in a chloroquine-resistant strain of *Plasmodium falciparum* is disclosed in Chemical Abstracts, Volume 69: 50900p (1968). Primaquine diphosphate, pyrimethamine and sulfadiazine were said to show causal prophylactic activity against rodent malaria, *Plasmodium berghei yoelii*, as disclosed in Chemical Abstracts, Volume 77: 109339h (1972). A three component composition of pyrimethamine, sulfadiazine and cycloguanil-HCl for treating rodent malaria is disclosed in Chemical Abstracts, Volume 96: 40845t (1982). Similarly, sulfadiazine sodium has been used to enhance the activities of certain antiinfective drugs against infections caused by pyrimethamine-susceptible or pyrimethamine-resistant strains of *P. falciparum* and *P. vivax* in owl monkeys. See, Chemical Abstracts, Volume 92: 15581p (1980).

There are a number of articles describing the treatment of *Toxoplasma gondii* with pyrimethamine and sulfadiazine, but at a ratio that uses a very large amount of sulfadiazine relative to pyrimethamine. See, e.g., Chemical Abstracts, Volume 78: 52708s (1973) (1 mg/kg pyrimethamine and 100 mg/kg sulfadiazine for mice); Chemical Abstracts, Volume 85: 72303d (1976)(2 mg/kg pyrimethamine and 100 mg/kg sulfadiazine for cats); Chemical Abstracts, Volume 99: 133330y (1983); Chemical Abstracts, Volume 101: 87339t (1984); Chemical Abstracts, Volume 122: 45806w (1995) (1 mg/kg pyrimethamine and 50 mg/kg sulfadiazine for monkeys); Chemical Abstracts, Volume 122: 253089n (1995). Chemical Abstracts, Volume 123: 102131u (1995) describes the daily administration of 25 mg pyrimethamine and a total of 2 g sulfadiazine to prevent toxoplasmic encephalitis relapse in AIDS patients.

The patent literature includes many descriptions of methods for treating protozoan-mediated diseases. McHardy, in U.S. Pat. No. 5,273,970, states that a protozoal disease, toxoplasmosis, may be controlled to a certain extent using pyrimethamine together with a sulfonamide. This patent asserts that baquiloprim can be used for the treatment and/or prophylaxis of protozoal infections in animals, including humans. Although the baquiloprim can be used as the sole active ingredient, it can be co-administered with a sulfonamide. A long list of suitable sulfonamides is provided, most preferably sulfadiazine, sulfamethoxazole, sulfadimethoxine, sulfadoxine, sulfamoxole, or sulfadimidine.

In U.S. Pat. No. 4,599,416, granted to Kompis, a process for the preparation of aqueous compositions of sulfonamides and sulfonamide potentiators for the treatment of bacterial infections in humans and animals is described. A long list of potential sulfonamides is provided. The "potentiators" are described as denoting compounds that increase the antibacterial activity of sulfonamides more than additively. An equally long "laundry" list of such potentiators is provided, which includes trimethoprim and pyrimethamine. Other patents dealing with protozoan parasites include: U.S. Pat. No. 4,293,547, granted to Lewis et al. for the treatment of malaria; U.S. Pat. No. 4,340,609, granted to Chou (various protozoal infestations); U.S. Pat. No. 4,368,193, granted to Argoudelis et al. (malaria); U.S. Pat. No. 4,728,641, granted to Tubaro et al. (protozoal infections generally); U.S. Pat. No. 4,992,444, granted to Stevens et al. (trypanosomes and malaria); and U.S. Pat. No. 5,486,535, granted to Marr et al. (*Toxoplasma gondii*).

Beech, in *Veterinary Medicine/Small Animal Clinician*, pp. 1562–1566 (December 1974) described a condition in eight (8) horses with signs of neurological disorder. On the assumption that toxoplasmosis was involved, the author suggested that pyrimethamine and sulfadiazine, used successfully against toxoplasma in man, might be useful in horses.

Welsch, B. B. recommended the use of pyrimethamine (0.5 mg/kg), combined with a 20 mg/kg two-part mixture of sulfadiazine (16.7 mg/kg) and trimethoprim (3.3 mg/kg), to treat horses suffering from EPM. See, Welsch, B. B., in *The Compendium North American Edition, Equine*, Morris, D. D. (Ed.) (1991) pp. 1599–1602.

Two articles by Clark et al., which appeared in *American Journal of Veterinary Research*, Volume 53, Number 12, pages 2292–2295 and 2296–2299 (December 1992), discuss the pharmacokinetics of intravenously and orally administered pyrimethamine in horses. The first article, at page 2292, states that clinical reports indicate the possible value of treatment of horses with protozoal encephalomyelitis with pyrimethamine in combination with trimethoprim and sulfonamides. On the other hand, the second article, at page 2299, concludes that the oral administration of 1 mg pyrimethamine/kg once a day for 10 days apparently does not present a serious toxicological problem to horses.

Hence, despite a great deal of past and on-going effort, there remains an unfulfilled need for a treatment for EPM-afflicted equines, particularly horses, which is not only effective but is also convenient to administer to maximize compliance and reduce the emergence of resistant strains. In particular, prior compositions for the treatment of EPM involve three-component mixtures, including pyrimethamine, sulfadiazine and trimethoprim. Moreover, where prior compositions contained pyrimethamine and sulfadiazine as the active ingredients, such compositions used very small ratios of pyrimethamine to sulfadiazine limiting their effectiveness to treating malaria only and hampering their usefulness in other pathological conditions, like protozoan-mediated diseases, especially EPM. The fact is that there is currently no approved drug or drug combination for the treatment of EPM.

SUMMARY OF THE INVENTION

Quite surprisingly, it has now been discovered that an effective, convenient method of treating EPM is realized by the administration to an equine suspected of being afflicted with EPM of therapeutic amounts of pyrimethamine and a sulfonamide, preferably sulfadiazine. The relative weight ratio of pyrimethamine to the sulfonamide may range from about 1:10 to about 1:30, preferably, about 1:15 to about 1:25, and most preferably about 1:20 in the case of a composition comprising pyrimethamine and sulfadiazine.

It should be pointed out that the compositions of the present invention do not contain significant amounts of trimethoprim, certainly less than about two-thirds of the weight amount of sulfadiazine present. Preferably, the therapeutic compositions used for the treatment of EPM are substantially free of trimethoprim, most preferably having no trimethoprim at all. Similarly, the methods of the present invention do not rely on the presence of significant amounts of trimethoprim in effecting successful treatment of EPM, using substantially the pyrimethamine and a sulfonamide as the principal active ingredients against the pathologic agent, namely, the organism Sarcocystis neurona in EPM. Hence, the methods of the present invention do not include the co-administration of known therapeutic amounts of trimethoprim.

In a preferred embodiment of the invention, the afflicted equine, e.g., a horse, is given a daily dose of pyrimethamine, which is equivalent to about 0.8–1.2 mg per kg of equine, most preferably about 1.0 mg per kg. The subject is also given, concurrently for the greatest convenience, an amount per day of a sulfonamide, which is equivalent to about 15–30 mg per kg of equine, most preferably about 20 mg per kg. Once daily administration of the active ingredients, say every morning on an empty stomach, for at least about 3 months, preferably about 90–180 days, is sufficient to treat the infection. In some cases, however, the treatment regimen can last indefinitely, sometimes for the remaining life of the horse. For ease of administration, the therapeutic composition may be given orally (that is, by mouth).

It should be apparent that an object of the present invention is the treatment of equine protozoal myeloencephalitis or EPM by providing a veterinary composition comprising pyrimethamine and a sulfonamide, provided that the composition does not also include significant amounts of trimethoprim. By "not also include significant amounts of trimethoprim" means that any trimethoprim present in the veterinary composition should not reach any known therapeutic levels of trimethoprim, certainly not reaching an amount by weight, which is equivalent to about two-thirds the weight of the active sulfonamide, preferably less than about one-half and more preferably less than about one-third of the sulfonamide. Most preferably, the veterinary composition of the present invention (or the instant method of treatment of EPM) is substantially free of trimethoprim.

Convenient dosage formulations of the present invention are also contemplated, including solid and liquid forms, and unit dosage forms comprising about 0.3–0.7 gm pyrimethamine and about 6–14 gm sulfonamide, preferably about 0.5 gm pyrimethamine and about 10 gm sulfonamide.

These and other objects of the invention will become apparent to those of ordinary skill in the art, especially after consideration of the following detailed description of the preferred embodiments.

DETAILED DESCRIPTION OF THE PREFERRED EMBODIMENTS

The instant invention involves, in a preferred embodiment, the administration of an oral suspension, containing pyrimethamine and a sulfonamide, such as sulfadiazine, designed to overcome the shortcomings of currently available treatments of EPM and to provide a more effective drug combination for horses and other equines infected with an organism of the genus Sarcocystis. As previously mentioned, pyrimethamine may be given in a preferred dose of about 1 mg/kg equine with a sulfonamide in a dose of about 15 to 30 mg/kg. equine, preferably 20 mg/kg.

It has been found that a 30 mL dose of an oral suspension (such as that described, below) daily on an empty stomach will provide adequate dosing for the treatment of EPM that neither pyrimethamine nor sulfadiazine can treat alone. Since EPM is a protozoal infection of the central nervous system, the appropriate drug combination must penetrate to the CNS and treat the protozoal infection.

In general, the composition to be administered may comprise about 10–20 gm pyrimethamine and about 150–600 gm sulfonamide, preferably 200–400 gm sulfonamide, per liter of composition. The liquid or solid composition may be prepared in unit dosage form depending upon the minimum size of the equine. Such unit dosage forms comprise a relative weight ratio of pyrimethamine to sulfonamide in a range of about 1:15 to about 1:30, preferably about 1:20. Typically, the unit dosage forms contain about 0.3–0.7 gm of pyrimethamine and about 6–14 gm of sulfonamide, most preferably 0.5 gm pyrimethamine and about 10 gm sulfonamide.

The present invention has been found to successfully inhibit the growth of the organism Sarcocystis neurona in equines, such as mules, ponies and horses. It has been observed that the preferred sulfonamide, sulfadiazine, has resulted in better than about a 70% rate of efficacy. In fact, the effectiveness of the present compositions and methods appears to be at least about 80% or 90% of the cases, and probably even higher.

In line with the foregoing, it is within the contemplation of the present invention to employ compositions utilizing one or more sulfonamides and/or pyrimidine derivative in treating EPM. Examples of other suitable pyrimidine derivatives include, but are not limited to, 2,4-diamino-5-benzylpyrimidines substituted in the phenyl ring, such as 2,4,diamino-5-(3,5-dimethoxy-4-methoxyethoxybenzy)-pyrimidine(tetroxoprim) and 2,4-diamino-5-(3,5, dimethoxy-4-methylthiobenzyl)-pyrimidine(metioprim). Still other useful pyrimidines may be 2,4-diamino-5-(4-bromo-3,5-dimethoxybenzyl)-pyrimidine, 2,4-diamino-5-[3,5-diathoxy-4-(pyrrol-1-yl)-benzyl]-pyrimidine, 2,4-diamino-5-(3,5-dimethoxy-4-dimethylaminobenzyl)-pyrimidine, 2,4-diamino-5-(3,4-dimethoxybenzyl)-pyrimidine (diaveridine) and 2,4-diamino-5-(2-methyl-4,5-dimethoxybenzyl)-pyrimidine.

In a similar manner, numerous sulfonamides may be suitably utilized in the present invention, including those previously disclosed in U.S. Pat. No. 5,273,970, whose disclosure is incorporated in its entirety by reference herein. In particular, those sulfonamides having a dinitrogen aromatic ring are especially useful, such as acetyl sulfamethoxypyrazine, N-2-formylsulfisomidine, salazosulfadimidine, sulfachlorpyridazine, sulfadimethoxine, sulfadoxine, sulfalene, sulfamerazine, sulfameter, sulfamethazine, sulfamethomidine, sulfamethoxypyridazine, sulfaperine, sulfaphenazole, sulfapyrazine and sulfisomidine.

Still other sulfonamides known to be useful in veterinary applications can be adventitiously used, including phthalylsulfacetamide, phthalylsulfathiazole, succinylsulfathiazole, sulfabenzamide, sulfacetamide, sulfaethidole, sulfaguanidine, sulfamethizole, sulfamethoxypyridazine, sulfanilamide, sulfanilamidomethanesulfonic acid triethanolamine salt, sulfanitran, sulfapyridine, sulfathiazole and sulfisoxazole. The above-mentioned sulfonamides may be used in place of the preferred sulfadiazine or in addition thereto.

The present compositions may be administered by routes well known to those skilled in the veterinary and formulation sciences. Therefore, although the pyrimethamine and sulfadiazine, for example, are conveniently administered orally, depending on the circumstances, the pharmaceutical composition may be administered parentally, topically, intramucosally (e.g., intravaginally), or by other routes known to those skilled in this art.

Compositions suitable for oral administration, in addition to suspensions, include tablets, capsules, gels, pastes, boluses, or preparations in the form of powders, granules, or pellets. Preferred orally administered compositions- include suspensions and tablets.

Alternatively, the composition may be administered parenterally by sub-cutaneous, intramuscular, intraperitoneal, or intravenous injection, or by implantation. The composition can be given as an intramammary injection whereby a suspension or solution is introduced into the udder.

Pharmaceutically acceptable carriers present in the compositions of the present invention are materials recommended for the purpose of administering the medicament. These may be liquid, solid, or gaseous materials, which are otherwise inert or medically acceptable and are compatible with the active ingredients. The same applies for any added excipients.

For oral administration, fine powders or granules will contain diluting agents, for example, calcium carbonate, calcium phosphate, mineral carriers, etc., disbursing and/or surface active agents, for example, polysorbates, and may be presented in a drench, in water or in a syrup, in a bolus, paste, or in capsules or sachets in the dry state or in a non-aqueous suspension, or in a suspension in water or syrup. Where desirable or necessary, preserving, suspending, thickening or emulsifying agents can be included. If intended for oral use, a bolus will be provided with retention means to inhibit regurgitation. For example, it may be weighed with a heavy density materials such as iron or tungsten or the like or may be retained by its shape, for example, by wings which spring after administration. Boluses may contain disintegrating agents such as maize starch or calcium or sodium methylcelluloses, hydroxypropylmethylcellulose, guar based vegetable gums, sodium alginates or sodium starch glycolates; granulating or binding agents, such as starch in the form of mucilage, starch derivatives, such as methylcellulose, calcium stearate, talc, gelatin or polyvinylpyrrolidone; and/or lubricating agents, such as magnesium stearate or stearic acid.

Other compounds which may be included are for example, medically inert ingredients, e.g. solid and liquid diluents, such as starch or calcium phosphate for tablets, boluses or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; dedusting agents such as liquid paraffin, fixed oils and surfactants and other therapeutically acceptable accessory ingredients, such as humectants, preservatives, buffers, and anti-oxidants, which are useful as carriers in such formulations. When desired, other medicaments and/or nutrients, such as vitamins or the like, unless contraindicated, may also be included.

It is also to be understood that while the preferred formulation is administered once a day, it may be given two or more times a day, depending on the circumstances. It should be understood that while it is convenient to administer the pyrimidine and sulfonamide concurrently, they can be given separately with equal efficacy. However, the other optimum conditions, such as the administration of the drug combination on an empty, preferably at least about one hour before the horse is fed should be observed.

A further appreciation of the invention may be gleaned from the following specific examples. These specific examples are provided for illustration only and are not to be regarded as restricting the invention in any way.

EXAMPLES

Veterinary compositions effective for the general treatment of EPM are provided, below, in the form of an oral suspension. The amounts of each component are based on a liquid suspension having a total volume of about 1 liter. As mentioned above, a useful dosage, e.g., for a 1,000 pound horse infected with Sarcocystis neurona (as evidenced by the presence of the protozoan in a sample from the subject's cerebrospinal fluid) is about 30 mL of the suspension, once a day, given on an empty stomach in the morning.

| Formulation A | |
|---|---|
| Component | Per Liter |
| 1. Sulfadiazine Base, USP | 166.67 g |
| 2. Sulfadiazine Sodium, USP | 166.67 g |
| 3. Pyrimethamine, USP | 16.67 g |
| 4. Sodium Benzoate, NF | 2.22 g |
| 5. Xanthan gum, NF | 1.11 g |
| 6. Aspartame, NF | 11.11 g |
| 7. Saccharin, NF | 2.78 g |
| 8. Yerba santa (eriodictyon californicum) | 55.56 mL |
| 9. Caramel flavoring, NF | 5.56 mL |
| 10. Polysorbate 80, NF | 6.67 mL |
| 11. Purified water, USP | q.s. to 1,000 mL |

Preferably, the composition does not contain substantial amounts of natural sugars. Most preferably, the composition is substantially free of natural sugars as some of the sulfonamides may be sensitive to the presence of naturally occurring sugars. Optionally, folic acid may also be administered to the subject, either concurrently or at a separate time. Typically, the subject may receive about 40 mg of folic acid per 500- to 1000-pound equine.

A stepwise procedure for the preparation of the oral suspension is provided below:

1. Weigh out the powders and triturate from the smallest quantity of powder to the largest quantity of powder, so that all powders are evenly mixed together.
2. In a separate container mix all the liquids and add half the volume of water needed for one liter.
3. Mix together the materials prepared in steps 1 and 2 in a large container and q.s. to one 1,000 liter with the remaining water.
4. Beat the suspension on a micronizer for five minutes, being certain said suspension is evenly mixed.
5. Package the final product and refrigerate when not in use. The suspension should be shaken well prior to use.

As further illustrations of the composition of the invention, the following descriptions of suitable alternative formulations are provided.

| Formulation B | |
|---|---|
| Component | Per Liter |
| 1. Sulfadiazine Sodium, USP | 333.34 g |
| 2. Pyrimethamine, USP | 33.34 g |
| 3. Sodium Benzoate, NF | 2.22 g |
| 4. Xanthan gum, NF | 5.0 g |
| 5. Nutrasweet, NF | 10.0 g |
| 7. Caramel flavoring, NF | 5.56 mL |
| 8. Polysorbate 80, NF | 6.67 mL |
| 9. Purified water, USP | q.s. to 1,000 mL |

The preceding formulation provides an easy to use paste.

| Formulation C | |
|---|---|
| Component | Per Liter |
| 1. Sulfamethoxazole, USP | 333.34 g |
| 2. Pyrimethamine, USP | 33.34 g |
| 3. Sodium Benzoate, NF | 2.22 g |
| 4. Xanthan gum, NF | 1.11 g |
| 5. Nutrasweet, NF | 10.0 g |
| 7. Caramel flavoring, NF | 5.56 mL |
| 8. Polysorbate 80, NF | 6.67 mL |
| 9. Purified water, USP | q.s. to 1,000 mL |

| Formulation D | |
|---|---|
| Component | Per 1000 g |
| 1. Sulfadiazine Base, USP | 333.34 g |
| 2. Pyrimethamine, USP | 16.67 g |
| 3. Sodium Benzoate, NF | 2.22 g |
| 4. Nutrasweet, NF | 10.0 g |
| 5. Lactose, NF | 638.11 g |

| Formulation E | |
|---|---|
| Component | Per 1000 g |
| 1. Sulfadoxine Base, USP | 300.06 g |
| 2. Pyrimethamine, USP | 16.67 g |
| 3. Sodium Benzoate, NF | 2.22 g |
| 4. Nutrasweet, NF | 10.0 g |
| 5. Lactose, NF | 671.39 g |

The preceding two formulations provide powders, which can be conveniently divided into individual packets, each containing 30 g of the inventive composition.

| Component | Per Liter |
|---|---|
| Formulation F | |
| 1. Sulfamoxole, USP | 333.34 g |
| 2. Pyrimethamine, USP | 13.34 g |
| 3. Sodium Benzoate, NF | 2.22 g |
| 4. Xanthan gum, NF | 5.0 g |
| 5. Nutrasweet, NF | 15.0 g |
| 7. Caramel flavoring, NF | 10.56 mL |
| 8. Polysorbate 80, NF | 6.67 mL |
| 9. Purified water, USP | q.s. to 1,000 mL |
| Formulation G | |
| 1. Sulfadimethoxine, USP | 500.10 g |
| 2. Pyrimethamine, USP | 16.67 g |
| 3. Sodium Benzoate, NF | 2.22 g |
| 4. Xanthan gum, NF | 5.0 g |
| 5. Nutrasweet, NF | 10.0 g |
| 7. Caramel flavoring, NF | 5.56 mL |
| 8. Polysorbate 80, NF | 6.67 mL |
| 9. Purified water, USP | q.s. to 1,000 mL |

Only the preferred embodiments of the invention and but a few examples of its versatility are shown and described in the present disclosure. It is to be understood that the invention is capable of use in various other combinations and environments and is capable of changes and modifications within the scope of the inventive concept as expressed herein. For example, the active ingredients of the contemplated veterinary composition can simply be mixed in an aqueous medium to provide a mixture that can be administered to the affected equine, usually by mouth.

What is claimed is:

1. A method of treating equine protozoal myeloencephalitis (EPM) comprising administering to an equine suspected of suffering from EPM therapeutically effective amounts of pyrimethamine and a sulfonamide, provided that if the sulfonamide is sulfadiazine, an amount of trimethoprim is not also administered, which amount of trimethoprim is 20 percent by weight of the amount of the sulfadiazine administered.

2. The method of claim 1 in which the pyrimethamine and sulfonamide are administered substantially concurrently.

3. The method of claim 1 which does not include the co-administration of trimethoprim.

4. The method of claim 1 which comprises administering the pyrimethamine and the sulfonamide orally.

5. The method of claim 4 which comprises the daily administration of the pyrimethamine and the sulfonamide.

6. The method of claim 1 which comprises administering a therapeutically effective amount of a composition comprising the pyrimethamine and the sulfonamide, provided that if the sulfonamide is sulfadiazine the composition does not also include an amount of trimethoprim which is 20 percent by weight of the amount of the sulfadiazine present in the composition.

7. The method of claim 6 the composition comprises the pyrimethamine and the sulfonamide in a relative weight ratio of about 1:10 to about 1:30.

8. The method of claim 1 which inhibits the growth of an organism from the *Sarcocystis neurona*.

9. The method of claim 1 which is effective in at least about 70% of the cases.

10. The method of claim 1 in which the sulfonamide is sulfadiazine.

11. The method of claim 1 in which the sulfonamide is selected from the group consisting of sulfachlorpyridazine, sulfadimethoxine, sulfamerazine, sulfamethazine, sulfamethoxypyridazine, sulfaphenazole, sulfapyrazine and sulfisomidine.

12. The method of claim 1 in which the pyrimethamine is administered in a daily dosage of about 1 mg/kg of equine.

13. The method of claim 1 in which the sulfonamide is administered in a daily dosage of about 15 to about 30 mg/kg of equine.

14. The method of claim 13 in which the sulfonamide is administered in a daily dosage of about 20 mg/kg of equine.

15. The method of claim 1 in which treatment is continued for at least about three months.

16. The method of claim 1 which further comprises administering folic acid.

17. The method of claim 16 in which the folic acid is administered daily at a dosage of about 40 mg per 1000-pound equine.

18. The method of claim 1 in which the pyrimethamine and the sulfadiazine are administered in a liquid form.

19. The method of claim 1 in which the pyrimethamine and the sulfadiazine are administered in the form of a solid.

20. A veterinary composition in unit dosage form for the treatment of equine protozoal myeloencephalitis (EPM) comprising pyrimethamine and a sulfonamide in a relative weight ratio of about 1:10 to about 1:30, respectively, provided that if the sulfonamide is sulfadiazine the composition does not also include an amount of trimethoprim which is 20 percent by weight of the amount of the sulfadiazine present in the composition.

21. The composition of claim 20 in which the sulfonamide is sulfadiazine.

22. The composition of claim 21 which is in the form of an oral suspension.

23. The composition of claim 22 which comprises about 10–20 gm pyrimethamine and about 150–600 gm sulfonamide per liter of composition.

24. The composition of claim 23 which comprises about 10–20 gm pyrimethamine and about 200–400 gm sulfonamide per liter of composition.

25. The composition of claim 22 which does not include substantial amounts of natural sugars.

26. The composition of claim 20 in which the pyrimethamine and the sulfonamide are present in a relative weight ratio of about 1:15 to about 1:25, respectively.

27. The composition of claim 20 in which the pyrimethamine and the sulfonamide are present in a relative weight ratio of about 1:20, respectively.

28. The composition of claim 20 in which the unit dosage comprises about 0.3–0.7 gm pyrimethamine and about 6–14 gm sulfonamide.

29. The composition of claim 28 in which the unit dosage comprises about 0.5 gm pyrimethamine and about 10 gm sulfonamide.

* * * * *